United States Patent [19]

Ishrak et al.

[11] Patent Number: 5,677,491
[45] Date of Patent: Oct. 14, 1997

[54] SPARSE TWO-DIMENSIONAL TRANSDUCER ARRAY

[75] Inventors: Syed Omar Ishrak, Santa Clara; Mehmet Salahi, San Jose; Farhad Towfiq, Santa Clara; Alan Chi-Chung Tai; Ha Thanh Pham, both of Milpitas, all of Calif.

[73] Assignee: Diasonics Ultrasound, Inc., Santa Clara, Calif.

[21] Appl. No.: 645,050

[22] Filed: May 14, 1996

Related U.S. Application Data

[63] Continuation of Ser. No. 287,225, Aug. 8, 1994, abandoned.
[51] Int. Cl.⁶ .................. G01N 29/00; H01L 41/04; A61B 8/14
[52] U.S. Cl. .................. 73/641; 73/628; 73/642; 310/335; 128/662.03
[58] Field of Search .................. 73/641; 310/335

[56] References Cited

U.S. PATENT DOCUMENTS

| | | | |
|---|---|---|---|
| 4,371,805 | 2/1983 | Diepers et al. | 310/334 |
| 4,401,910 | 8/1983 | Beerman | 73/642 |
| 4,580,451 | 4/1986 | Miwa et al. | 128/661.01 |
| 4,670,683 | 6/1987 | t'Hoen | 310/334 |
| 4,694,434 | 9/1987 | Von Ramm et al. | 73/626 |
| 4,730,495 | 3/1988 | Green | 73/620 |
| 4,893,624 | 1/1990 | Lele | 128/399 |
| 5,050,588 | 9/1991 | Grey et al. | 128/662.03 |
| 5,060,651 | 10/1991 | Kondo et al. | 73/628 |
| 5,127,410 | 7/1992 | King et al. | 128/662.03 |
| 5,186,175 | 2/1993 | Hirama et al. | 128/661.01 |
| 5,249,577 | 10/1993 | Shinomura et al. | 73/626 |
| 5,490,512 | 2/1996 | Kwon et al. | 128/661.01 |

Primary Examiner—Hezron E. Williams
Assistant Examiner—Richard A. Moller
Attorney, Agent, or Firm—Blakely, Sokoloff, Taylor & Zafman

[57] ABSTRACT

A two-dimensional ultrasonic transducer for forming images. The transducer has a plurality of transducer elements for producing ultrasonic bursts in a predetermined manner, and receiving reflected ultrasound from the subject under examination due to the ultrasonic bursts. The plurality of transducer elements are arranged in an array into columns and rows, the columns of the transducer elements arranged in a scanning plane for scanning the subject under examination in order to form a two-dimensional profile of the subject, and the rows of the transducer elements having groups of symmetrically arranged transducer elements being oriented in a elevational plane. Each of the groups of symmetrically arranged transducer elements are mechanically arranged to have a focus at specified locations distant from the transducer which is within the subject under examination. Each of the groups of symmetrically arranged transducer elements coupled to a conductive channels for activating the group of symmetrically arranged transducer elements simultaneously to focus one of the ultrasonic bursts at the specified location from the transducer, and receive signals from the transducer elements due to received ultrasonic echoes due to the ultrasonic bursts. In certain embodiments, the mechanical arrangement of the groups of transducers comprises a lens affixed to the transducer elements in order to focus the ultrasonic bursts at the specified locations.

14 Claims, 16 Drawing Sheets

Aperture (Path Length) Error

One-Dimensional Array

SPARSE TWO-DIMENSIONAL TRANSDUCER ARRAY

This is a continuation of application Ser. No. 08/287,225, filed Aug. 8, 1994, now abandoned.

BACKGROUND OF THE INVENTION

1. Field of the Invention

The present invention relates to the field of imaging by means of ultrasonic examination. More specifically, the present invention relates to a sparse two-dimensional transducer array for forming ultrasonic images which has predefined foci in the elevational plane at certain positions by means of a compound lens.

2. Background Information

A variety of prior art apparatus have been used for forming two-dimensional images of a subject under examination using ultrasonic imaging systems. Typically, such systems employ ultrasonic probes in a variety of configurations in order to generate ultrasonic reference pulses or "bursts" into the subject under examination, and receive reflected ultrasound due to these ultrasonic bursts. A variety of probe designs has been used. For example, early systems employed fixed-focus transducers which employed either a lens or an acoustic mirror for focusing the ultrasonic bursts and receiving the ultrasound due to the burst within the subject under examination. Of course, such fixed-focus apparatus suffered from defects such as the ability to change focus to focus at a variety of depths, and the ability to generate a high-quality two-dimensional image (profile) of the subject under examination. Other transducer designs were created over time in order to address these problems.

Mechanical probe designs used a single or a plurality of transducer elements moved in a predetermined fashion by mechanical means (e.g., a motor) in order to accomplish scanning in a scanning plane. Single element transducers had a fixed focus at a single depth in the scanning plane. Another type of transducer used in the prior art is known as the annular array wherein a plurality of ring-shaped transducer elements is arranged on the probe in a concentric fashion. The signals to and from each ring are provided with different electronic time delays, so as to focus the beam at different depths. Annular arrays provide focusing both in the scanning plane and in the elevational or thickness plane of the image. Because of variances in motor speed, and the upper physical limitations of scanning in such a design, such mechanical probes (both single element and annular array) have several constraints. The chief constraints of mechanical probes is that beam agility is not available. This means that the beam cannot instantaneously move from one point to another in the scanning plane, and speed is limited by the motor design. Because of this limitation, multiple transmit zones in B-scan Imaging and simultaneous Duplex Doppler have never been achieved with mechanical probes. Also Color Flow Imaging has been implemented using these designs only with limited success.

A last type of transducer probe is known as the one-dimensional transducer array. Typically, this type of probe comprises a plurality of transducer elements arranged in a single-dimensional array wherein the array is used for scanning and electronic focusing, in order to form a two-dimensional profile of the subject under examination, rather than using annular arrays or single-element designs. This provides a higher-quality two-dimensional profile of a subject under examination. However, it does have its limitations. Some of these limitations will now be discussed.

FIG. 1 illustrates a transducer probe which comprises a single pre-focused receiving and transmitting surface 100 which is used for generating an ultrasonic burst and receiving echoes from all depths to a focus A, a predetermined distance from surface 100. For any emissive surface or aperture with a focus at a position A, whether the focus is achieved electronically or by means of a fixed-focus transmissive surface, path length errors increase at a different rate for depths other than A depending on the size of the aperture. For example, at a position as shown in FIG. 1, or any other position than the actual focal point A, there is a reduction in the quality of the reflection. This is because, unlike focal point A, the path lengths of distances from all other positions to different points in the aperture of the emitting/receiving surface vary. For example, the path lengths $z_0$, $z_1$ and $z_2$ to depth B are all different from various points $a_0$, $a_1$ and $a_2$ on surface 100. These varying path lengths, known as aperture path length error, result in image degradation. For example, when using an aperture having endpoints $a_1$ for surface 100, the path length error is the difference between the distances $z_1$ and $z_0$. An aperture having the endpoints $a_2$ on surface 100 will have a path length error=$z_2-z_0$. Thus, the greater the aperture for any depth other than the predetermined focus, the greater the aperture path length error. The phase error due to the path length errors (in degrees) is then defined as $$\frac{\text{path length error (mm)} \times 360°}{\text{wavelength (mm)}}.$$

Having a small aperture for any given focus minimizes aperture error, however, resolution is lost. Thus, there is a trade-off between aperture size to achieve optimum resolution and phase errors outside the focal point which cause degradation of an image and a reduced depth of focus.

This degradation caused by aperture error can be avoided by electronically adjusting the focus for every depth by changing the curvature of the transmissive surface for imaging a particular location. This is known as "dynamic focusing." This has the net effect of producing a larger zone in which the reflections received are all in focus. Such a surface can only be achieved by electronic means (e.g., delays in transmission of reference pulses for different regions of the surface, and delays in reception of ultrasound echoes due to the reference pulses). It is desirable to keep the number of readjustments of the focus to a minimum. During transmit mode, with every readjustment of focus, the frame rate decreases, because a new pulse has to be sent and received. In the receive mode, fewer readjustments require less complexity in the electronics. The less the aperture error outside the focal point, the fewer readjustments are needed to provide coverage over a given range of depths. Aperture error therefore, is something which needs to be contended with and compromises between frame rate and image quality need to be made.

Yet another error which may occur in certain transducers is known as element error. This type of error occurs in prior art one-dimensional arrays which focus the beam at various positions by means of electronic delays in emission of ultrasonic bursts from the elements in the array. Such an array is typically one-dimensional, for example, having n elements for scanning. Focusing of the beam is provided in the scanning plane only. An array which provides scanning is illustrated as 200 shown in FIG. 2a, and may form focus A by means of electronic delays in the activation of each of the transducer elements as illustrated in the cross-sectional view FIG. 2b. The wavefront, due to the delays in transmission, is shown as 202 in FIG. 2b. Of course, because the elements cannot be infinitesimally small, as in an ideal lens shown as 210 in FIG. 2b, a path length error known as "element error" occurs. The actual wavefront 202 caused by the delays is different from the ideal lens 210 as shown in FIG. 2b. Element error is the difference between the ideal transmissive surface of an element (represented by the ideal lens 210 focusing at depth A) and the wavefront achieved by the delays in the transmission of the bursts and reception of echoes at each of the transducer elements. In other words, it is the maximum difference of the path lengths across an element. For small size elements this error is small and the dominant error is the path length error across the aperture. For large size elements, path length errors over an element become more significant than aperture path length errors. For example, the element error for a particular transducer element 220 which is used for forming a signal due to the echo from focus A, there is an element path length error of the total of the distance between the ideal lens 210, and the actual wavefront 202 due to the electronic delays in the activation of the transducer elements. The differences between distances $z_2$ and $z_3$ are referred to as elevational path length error because an ideal lens has all path lengths (e.g., $z_2=z_3$) equal. The actual wavefront from one edge 223 of the element during transmit, and ideal lens at position 224 while focusing at depth A is thus referred to as an element delay error.

In addition to these element path length errors in the scanning plane, because of the inherent design of one-dimensional arrays, no focusing is generally provided in the "elevational plane" at all. However, the concepts of path length error across apertures and elements can be extended to an array with elements in the elevational plane. Similar problems occur on receive.

Yet another design which has been frequently used in prior art ultrasonic imaging systems is the annular array such as 300 illustrated in a front view in FIG. 3a. The annular array has a plurality of concentric ring-shaped transducer elements 301–304. The annular array has a pre-set mechanical focus at a fixed location from the face of the transducer such as C shown in the cross-sectional view of FIG. 3b. There are several advantages of such a design. First, elevational plane focusing of the same quality in the scanning plane is obtained because of the elements being shaped as rings instead of rectangles. Second, the focusing of the beam at depths other than the preset focus (e.g., depths A, B and D of FIG. 3b) is achieved with smaller element path length errors, at least in principle, by means of electronic delays as in one-dimensional arrays. However, although mechanical scanning capability is provided in such a design, (typically performed using a motor which mechanically rotates or oscillates the surface about a central axis) the limits of motor design reduces the utility of annular arrays. Due to the mechanical nature of the device, beam agility is also very limited.

A theoretical two-dimensional array would provide beam agility in the scanning plane and would also provide electronic focusing in the elevational plane. Such designs do not exist because a practical configuration employing 100 elements in the scanning plane, and 40 elements in the elevational plane would require a very large number of channels due to the very large number of elements (4000 separate transmit and receive channels). Even exploiting symmetrical connections in the elevational plane, the number of channels required for interconnection of these elements is still approximately 1500 to 2000 channels, which is well beyond current technology in transducer construction. Increasing the size of elements in the elevational plane may provide a partial solution to this problem, reducing the number of channels required, however, element errors for the different foci then become unacceptably large.

Thus, prior art transducers for ultrasonic imaging have fundamental shortcomings, in providing elevational plane electronic focusing.

SUMMARY AND OBJECTS OF THE PRESENT INVENTION

One of the objects of the present invention is to provide the capability for focusing ultrasonic bursts at a variety of depths in an elevational plane within a subject under examination, but yet, still provide electronic scanning and beam control capability.

Another of the objects of the present invention is to provide a transducer array which does not require a prohibitively large number of channels in order to form two-dimensional focusing of a subject under examination.

Another of the objects of the present invention is to provide a transducer design which minimizes aperture and element errors.

Another of the objects of the present invention is to alleviate certain of the shortcomings of prior art transducer designs such as those using annular or one-dimensional scanned arrays.

These and other objects of the present invention are provided for by a two-dimensional ultrasonic transducer for forming images (e.g. of a subject under examination). The transducer has a plurality of transducer elements for producing ultrasonic bursts in a predetermined manner, and receiving reflected ultrasound due to the ultrasonic bursts. The plurality of transducer elements are arranged in an array into columns and rows, the columns of the transducer elements arranged in a scanning plane for scanning the subject under examination in order to form a two-dimensional profile, and the rows of the transducer elements having groups of symmetrically arranged transducer elements being oriented in a elevational plane. Each of the groups of symmetrically arranged transducer elements in the elevational plane are mechanically arranged to have a focus at specified locations (more than one) distant from the transducer. Each of the groups of symmetrically arranged transducer elements coupled to conductive channels for activating the group of symmetrically arranged transducer elements simultaneously to focus one of the ultrasonic bursts at the specified locations from the transducer. They are also arranged to receive signals from the transducer elements in the form of received ultrasonic echoes due to the ultrasonic burst. In certain embodiments, the mechanical arrangement of the groups of transducers comprises a lens affixed to the transducer elements in order to focus the ultrasonic bursts at the specified locations, and in other embodiments, the mechanical arrangement includes lens-shaped transducers themselves for the different loci. Such a lens with multiple foci is known as a compound lens. Embodiments of the present invention also use "aperture growth" for imaging foci residing at more distant locations, including, an apparatus for activating centrally located groups of transducer elements simultaneously with groups of transducer elements located outside said centrally located groups of transducer elements. Thus, focusing of the far-field may be performed without any electronic delays, but rather by aperture growth only. The apparatus may also include a time delayed activation circuit for imaging focal zones (e.g., intermediate zones) other than those provided by the fixed focus of the compound lens.

Other objects, features and advantages of the present invention will be apparent from the description and figures which follow below.

BRIEF DESCRIPTION OF THE DRAWINGS

The present invention is illustrated by way of example and not limitation in the figures of the accompanying in which like references indicate like elements and in which.

DETAILED DESCRIPTION

The present invention describes a transducer design for use in ultrasonic imaging which addresses many of the deficiencies discussed above with respect to the prior art. Although the present invention will be discussed with reference to specific embodiments, it can be appreciated by one skilled in the art that these are for illustrative purposes only, and are not intended to limit the scope and subject matter of the present invention. It can be appreciated by one skilled in the art that many modifications may be made without departing from the overall spirit and scope of the present invention. It should also be noted that although only the design of the transducer will be discussed here and that such a device is to be used in conjunction with an ultrasonic imaging apparatus having a transmitter/receiver, control means and display which is used for providing an image of a subject under examination (e.g., a human patient). Such a transducer may be implemented in a variety of configurations for a variety of applications, e.g., color Doppler imaging, B-scan, etc., and the details of such systems are not required for an understanding of the present invention, as it is well-known to those skilled in the art.

Figure 1:
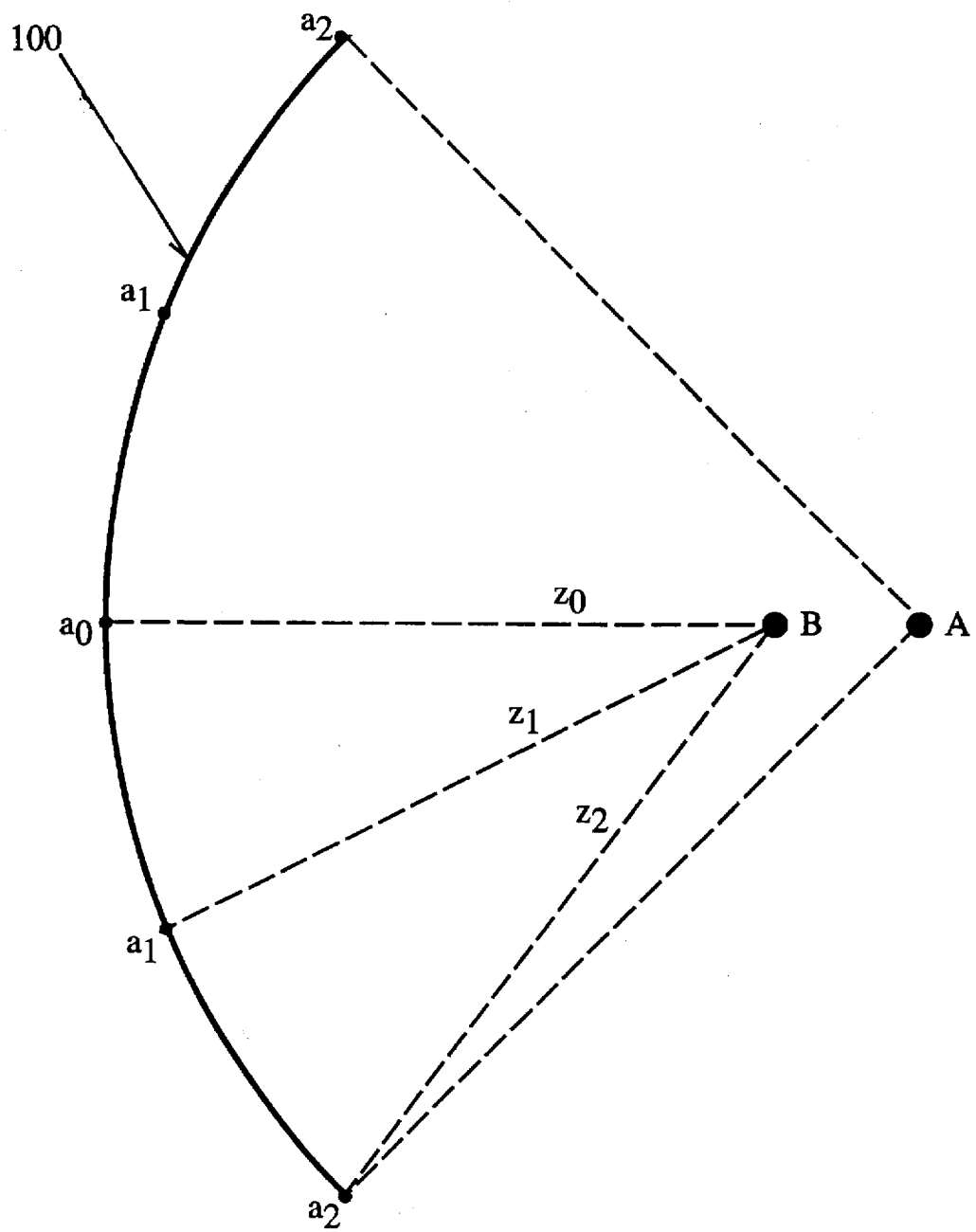
FIG. 1 illustrates aperture or "path length" errors which occur in the prior art.
Figure 2A:
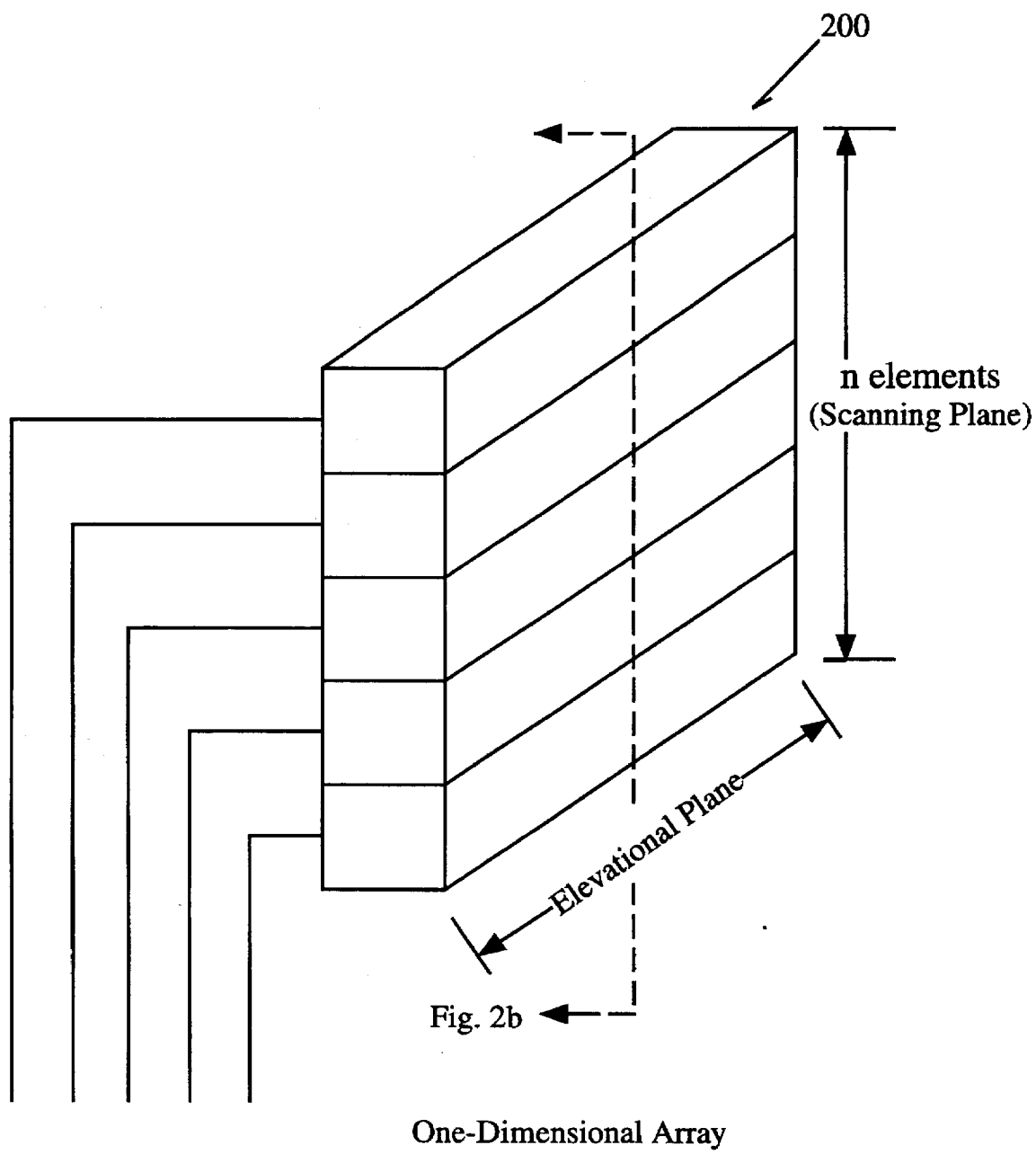
FIGS. 2a and 2b illustrate element errors which occur in typical prior art one-dimensional transducer arrays.
Figure 2B:
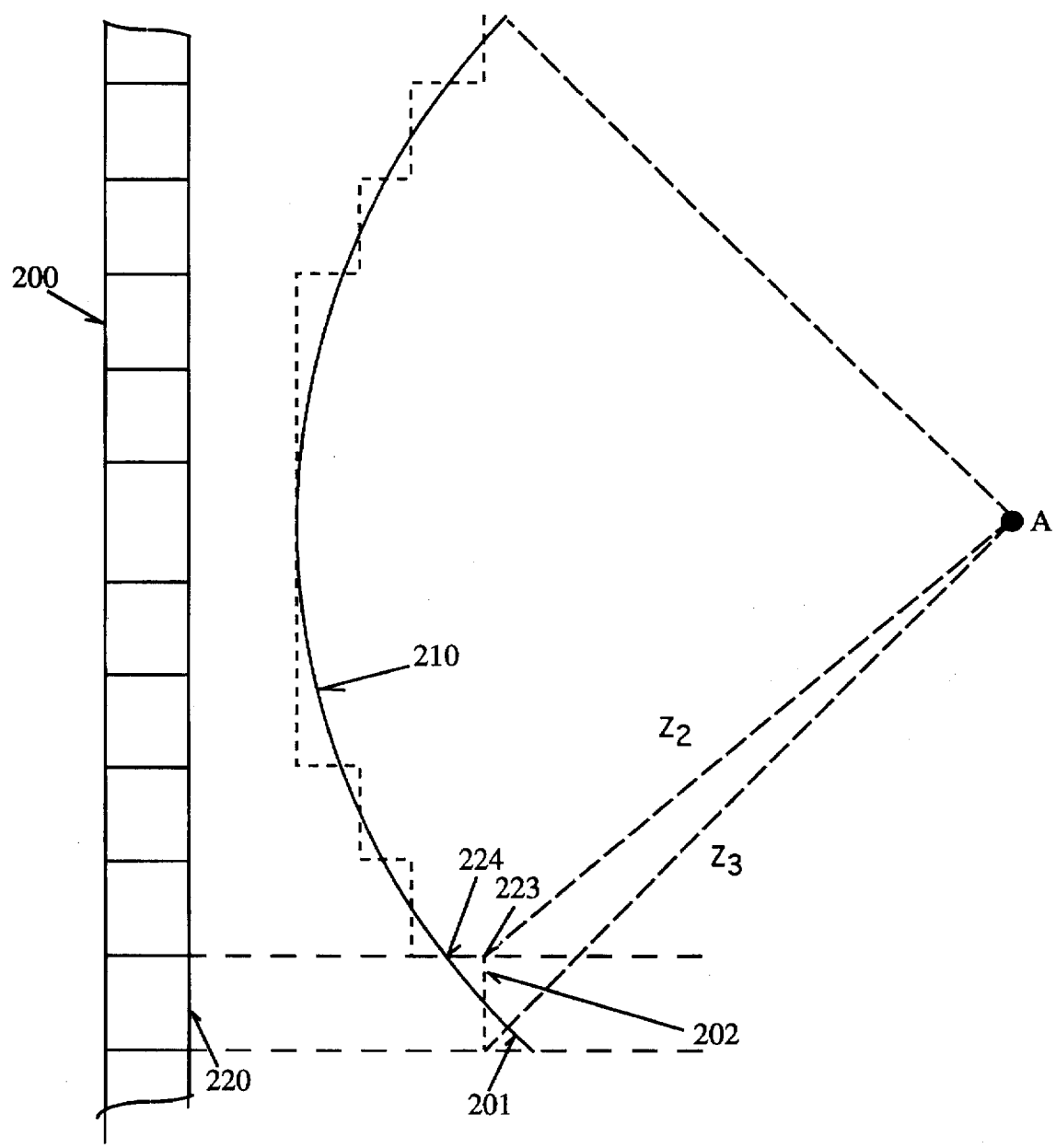
Figure 3A:
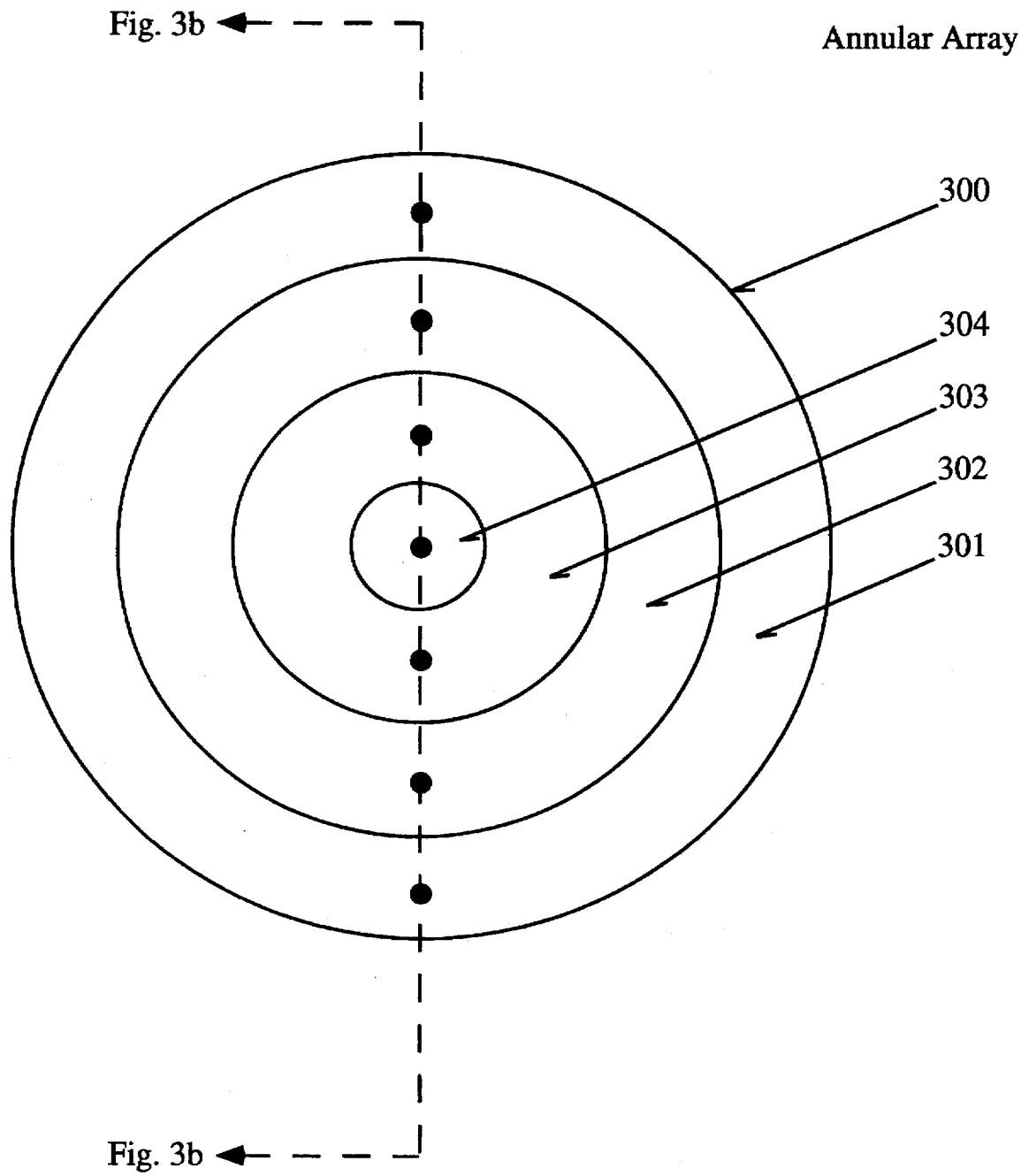
FIGS. 3a and 3b illustrate a prior art annular array.
Figure 3B:
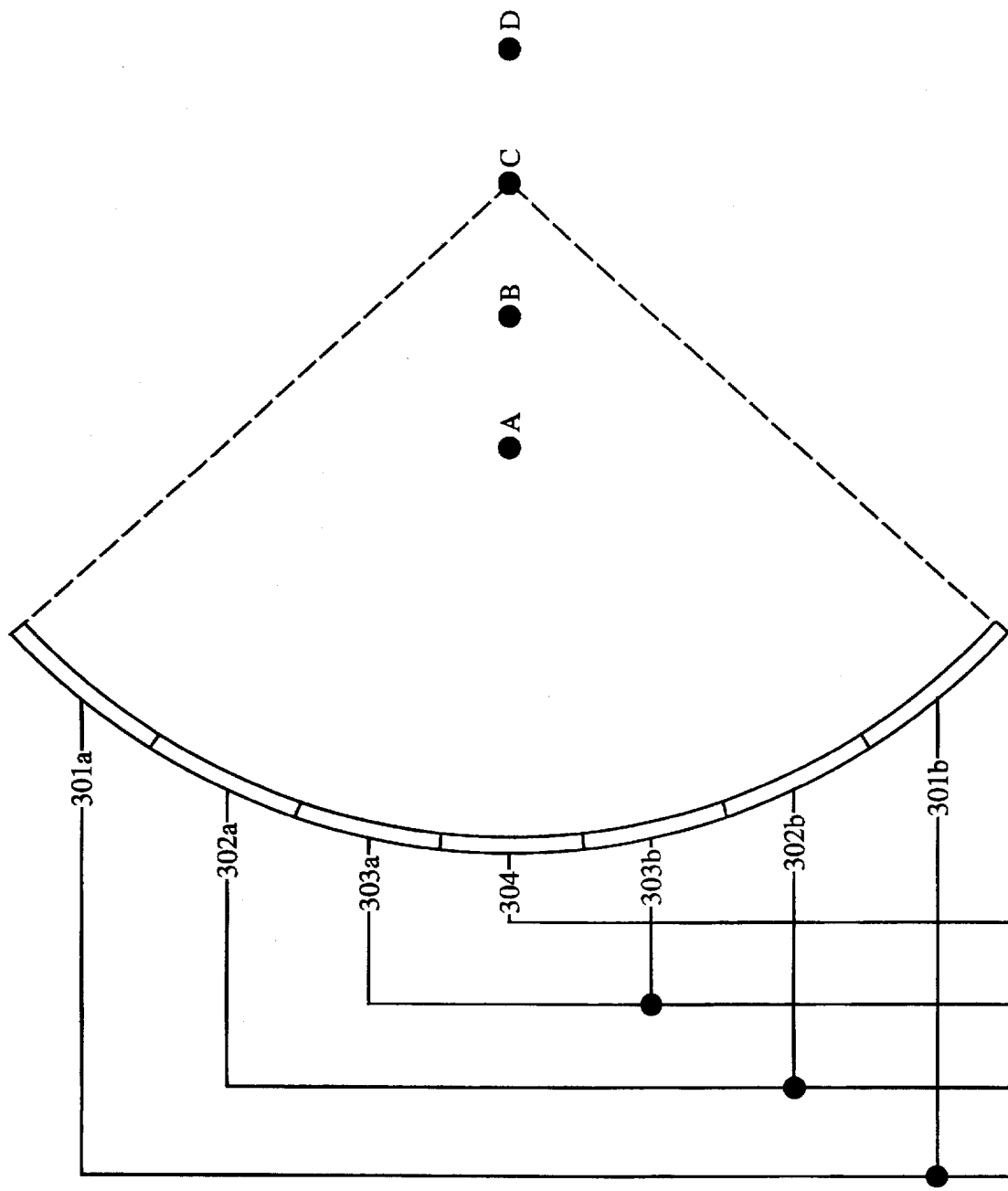
Figure 4A:
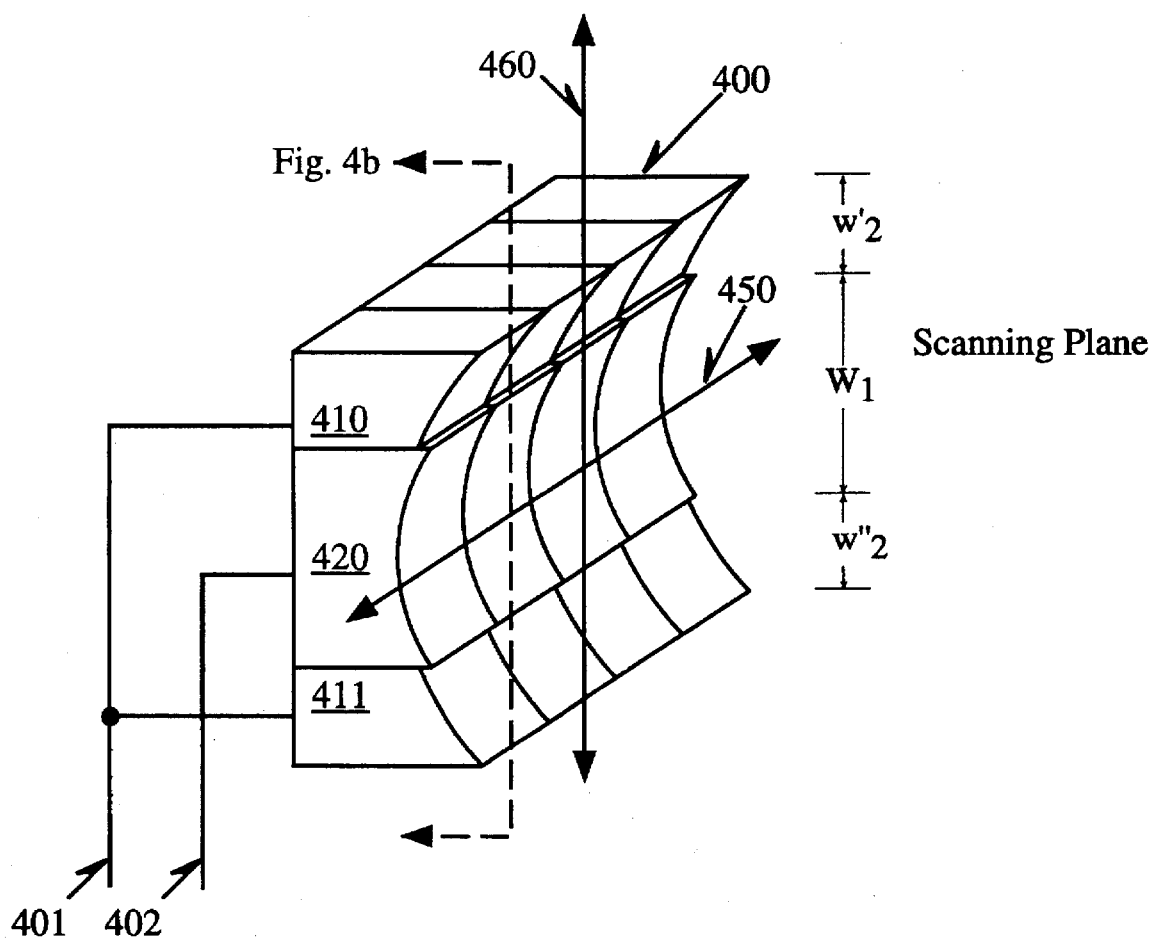
FIGS. 4a and 4b show a sparse two-dimensional transducer array in one embodiment of the present invention.
Figure 4B:
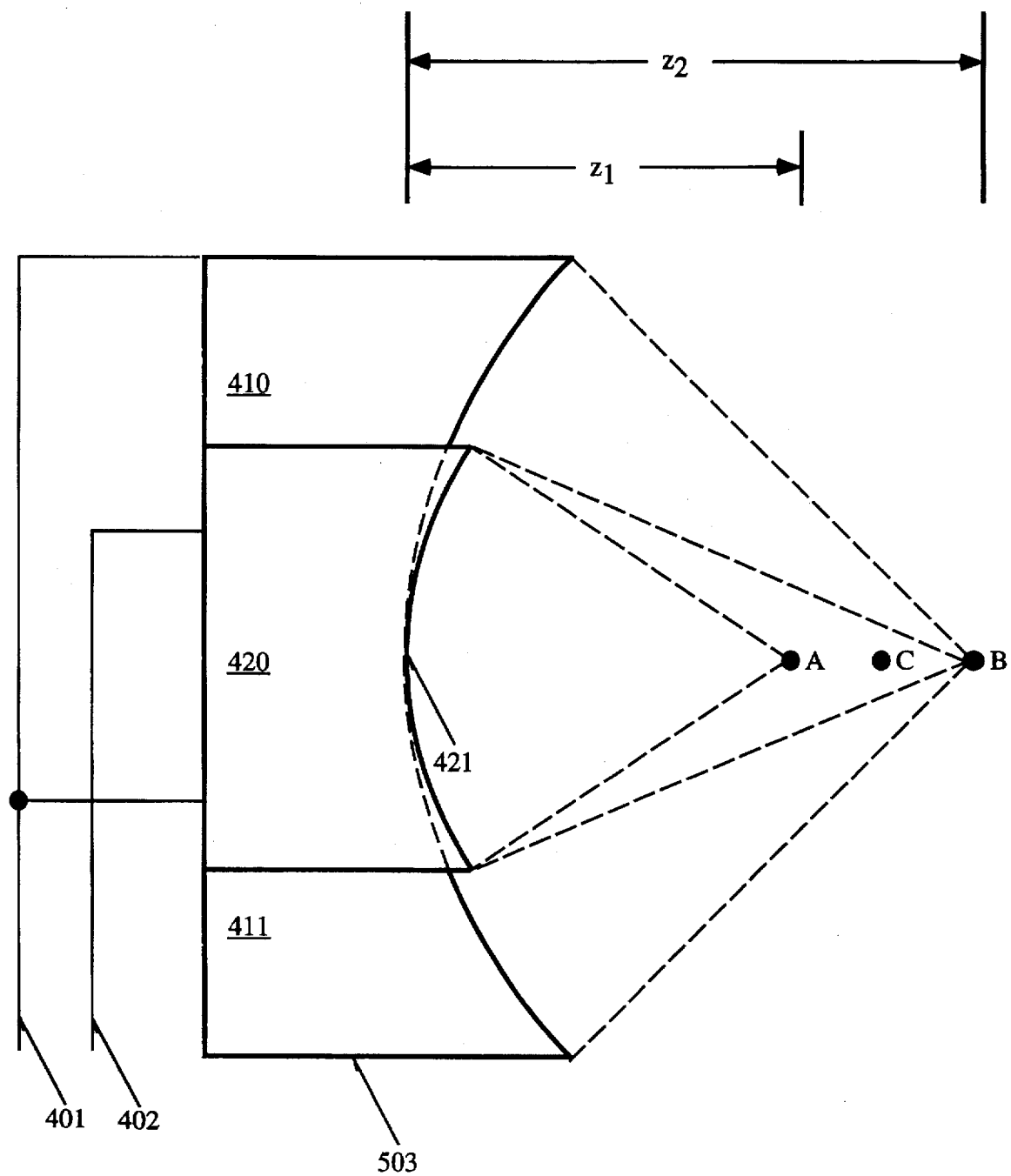

One embodiment of the present invention is illustrated in the perspective view of transducer array 400 of FIG. 4a. A cross-section view of array 400 is shown in FIG. 4b. Transducer 400 comprises a scanning transducer array which has a plurality of columns and rows wherein the rows are arranged in a scanning plane 450, and the columns of the transducer are arranged in an elevational plane 460 also known as the "out-of-plane." Although only a few elements for scanning are shown in the figure for illustration purposes (four in FIG. 4a) as many elements as required and/or practicable may be used (e.g., typically, 100 or more). Instead of focusing the energy in the elevational plane or a fixed location, as is typical in prior art one-dimensional arrays, the transducer array 400 of this embodiment of the present invention implements extended mechanical focusing of the array in the elevational plane 460. In some applications, electronic focusing may also be implemented in conjunction with the extended mechanical focusing in the elevational plane. Thus, for each column in the elevational plane 460, the transducer elements are constructed so as to have a different preset mechanical foci at predetermined locations. As illustrated, symmetric elements in the elevational plane are wired in parallel so that they may be activated in tandem, such as channel 401, during both transmit and receive cycles. There is a separate set of signal pairs for each scanning element. Prior art errors such as element error and aperture path length errors are minimized when used to image at certain foci using this design. These will be discussed in more detail with reference to the cross-section view of transducer 400 in FIG. 4b.

Yet another feature of transducer array 400 which is distinguishable from many of the prior art transducers discussed above, is that the number of "columns" of transducer elements for focusing in the elevational plane 460 is very limited. Thus, array 400 has two preset focal positions A (the near-field) and B (the far-field) in the elevational plane, requiring only two channels per scanning plane element for focusing the transducer array in elevational plane 460. Array 400 is therefore referred to as a "sparse" array because it has very few elements (in implemented embodiments—fewer than 10) in the elevational plane, rather than a very large number (e.g., 100) as in the scanning plane. In general, sparse arrays can be viewed as those which have elements with widths in the elevational plane approximately exceeding 4 times the wavelength of the reference pulse(s). In implemented embodiments of the present invention, the width of elements such as 410, 411 and 420 in the elevational plane are equal to 6 λ although this can vary according to implementation. Since certain elements in elevational plane 460 will be activated simultaneously for producing an ultrasonic burst which is focused at predetermined locations, certain symmetrical transducer elements are wired in parallel. Thus, for example, channel 401 is used for activating two symmetrical transducer elements in the array, and channel 402 is used for activating a single transducer element at the center of sparse array 400. This avoids the large numbers of channels which would normally be required for a two-dimensional array which would provide electronic focusing in the elevational plane. As many elements and corresponding symmetrically wired channels (two for each in this embodiment) as are required and/or practicable for scanning in scanning plane 450 are provided as required although only four are shown in FIG. 4a for illustration purposes.

As is shown in FIG. 4b, the parallel-wired transducer elements 410 and 411 have a pre-constructed cylindrical focus at the far-field focus B as is illustrated in FIG. 4b due to their shape. The single transducer element at the center of array 420 has a predetermined cylindrical focus at the near-field focus A as determined by its shape. As is apparent, the total width of the transducer elements 410 and 411 is much larger than that for the single transducer element 420. This embodiment is constructed so that the same F number is maintained for the preset depths. The F number for the focus A, residing at a position $z_1$ distant from the transducer face, is equal to $f_1=z_1/w_1$ (the ratio of the distance $z_1$ of the transducer face to the focus and the width $w_1$ of the transmissive surface). Transducer array 400 is designed so that all of the elements during a scan are activated for imaging at point B via activation of both channels 401 and 402. Thus, by means of aperture growth, the F number for the focus B is $$f_2 = \frac{z_2}{(w_2 + w_1)}$$

wherein $w_2 = w_2' + w_2''$ (the widths of each of the two transducer elements 410 and 411) and $z_2$ is the distance of the focus B from the emissive surface of transducer 400. In order to maintain the same F number when activating all of the transducer elements 410, 411 and 420 while imaging at far-field zone B, the total width of the transducer elements is increased in the elevational plane for each of the more distant foci. Thus:

$$\frac{z_1}{w_1} = \frac{z_2}{(w_1 + w_2)}.$$

In embodiments of the present invention which have more than two preset focal zones, the F number should remain approximately the same for all of the elements activated while imaging each preset zone. In implemented embodiments of the present invention, $w_1 = 4.8$ mm, $w_2 = 4.2$ mm, $z_1 = 1.68$ cm and $z_2 = 3$ cm. Thus, although the transducer shown in FIGS. 4a and 4b only has two focal zones, assuming that there are any number of focal zones and an equivalent number of element pairs, the aperture is increased in order for the same F number at the different preset focal zones of the transducer. Element (path length) errors are kept to a minimum due to the shapes of the elements while imaging either of the focal zones.

Because the shape of the elements in the elevational plane in the array more closely approximates that of an actual transmissive/receptive surface than a flat electronically focused transducer array, element errors are also substantially reduced. The mechanical shape of each transducer element almost precisely matches that of the ideal lens for the preset focal zones A and B. Element error is almost entirely reduced, improving image quality. Note also that the center of the cylindrical shape formed by elements 410 and 411 and the center of the cylinder defined by element 420 are constructed to coincide at position 421 in this embodiment. In alternative embodiments, elements 410, 411 and 420 may not have coincident centers, but rather, use electronic delays during transmit and receive to achieve the same result.

Note also because the coincident point 421 of the cylindrical focus formed by elements 420 and elements 410 and 411 aligns precisely, extended focusing at focal zone B by activating transducers 420, 410, and 411, may be performed by adding additional elements to the activated surface rather than by performing electronic focusing by delays in transmit and/or receive. Thus, extended focusing may be performed strictly by aperture growth, and no electronic delays in transmission or reception are required at all for elevational plane focusing. In effect, extended elevational focusing is thus provided with aperture growth only by adding additional elements to the active surface for imaging at deeper foci. This has unique advantages over prior art electronic focusing techniques, such as those used in one-dimensional arrays in the scanning plane, wherein complex beam-forming electronics are required for extended elevational plane focusing. No complex beam-forming electronics are required in this embodiment of the invention for elevational plane focusing in the far-field because of the coincident centers of the cylindrical foci of the elements. For imaging at intermediate regions (e.g., intermediate focal zone shown in FIG. 4b) performance may be further enhanced by using electronic focusing in conjunction with the design shown in FIGS. 4a and 4b. As discussed previously, a design not having coincident centers may be useful, however, the use of coincident centers of the lenses for the at least two preset focal zones has advantages over the prior art.

Note that although element 420, when activated, has a preset focus at focal zone A that at the center 421 of element 420 the path length errors within the element are zero while imaging at focal zone B. As we diverge from the center 421 of element 420, during focusing at zone B, the error for element 420 does increase minimally, however, it is still substantially less than a perfectly flat transmissive surface as in an electronically-focused array. Elements 410 and 411, in contrast, are perfectly focused at depth B. So, although the combined transmissive surfaces of transmissive elements 410, 411 and 420 is not a perfect replication of a lens having a focus at B, because of the constructed shape of element 420 in the elevational plane, the element error problems of the prior art are reduced. If a prior art transducer having the same elevational focus for both element 420 and elements 410 and 411 is used (i.e., no compound lens) and the elevational focus is chosen at point A, the element errors for elements 410 and 411 for focus at point B are also very large. The shape of the transducer in the elevational plane provides the advantages of multiple focal zones and electronic scanning without the large number of channels which would be required in a full two-dimensional array implementing electronic focusing. When focusing at zone A, elements 410 and 411 are not used at all, and the resulting image is in perfect focus because only element 420 is used for imaging.

Note that for a third focal zone, such as at an intermediate point C as illustrated in FIG. 4b, focusing may be accomplished by means of electronic delays in the transmission/reception periods of elements 410, 411 and 420. Although element path length errors of the three combined elements are greater than would occur at their preset focal zones A and B shown in FIG. 4b, that the element error for intermediate focal zone C shown in FIG. 4b is still less than that achieved exclusively by electronic focusing of flat transducer elements. The curved shape of the elements in the elevational plane provides less element error than would be achieved with electronic focusing of a perfectly flat surface, even at an intermediate focal zone. While focusing at zone C, the goal is to minimize aperture error. Element error while imaging at zone C, over positions A and B, however, it is still acceptably less than the prior art flat array or transducer having a single preset focus.

In addition to performing electronic focusing while imaging regions at various depths, the transmit and receive frequencies may be optimized for each particular depth. Apodization may also be Used for varying gain during transmit and receive for different depths according to application, and/or for different elements in the elevational plane because the different sections of elements in the elevational plane may be activated separately. For example, reducing the gain for outer elements in the array in the elevational plane while imaging at a particular depth may be useful for minimizing side lobes and increasing depth of field. For example, while activating center element 420 a first amplitude of reference pulse during transmit may be used and while activating all of elements 420, 410 and 411 may be activated with a second amplitude of the reference pulse. The first amplitude may be larger than the second amplitude to decrease side lobes in the far-field.

Figure 5A:
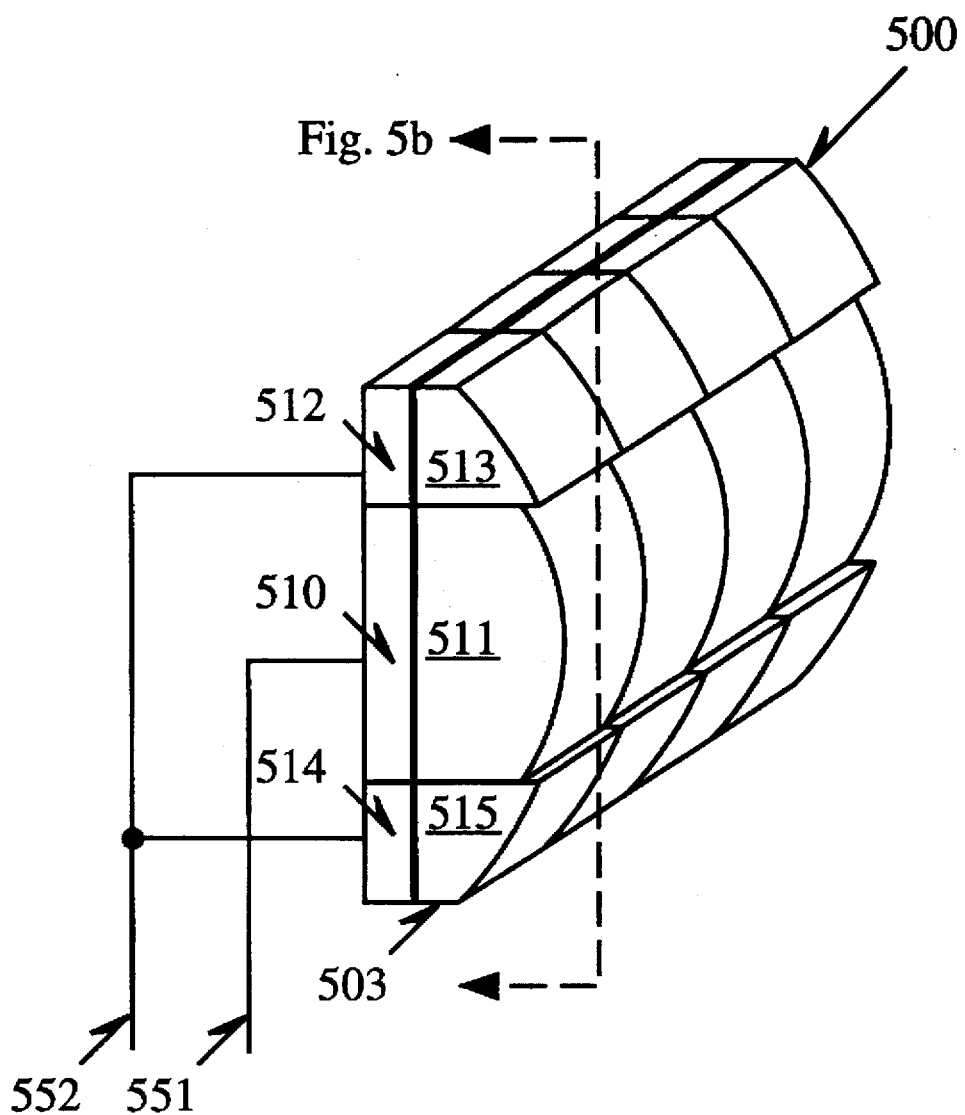
FIG. 5 shows a cross-section of an alternative sparse transducer array with an affixed compound lens.

500 of FIG. 5a shows a perspective view of an alternative embodiment of a sparse transducer array using a compound lens. In this embodiment of the invention, a plurality of transducers 510, 512, and 514 are focused by compound lens assembly 503 which is affixed to the transducer elements. These are shown in more detail in the cross-section view of FIG. 5b. As illustrated and discussed with reference to FIG. 4a above, although only four elements are shown in the scanning plane in transducer array 500, it can be appreciated by one skilled in the art that as many scanning elements as are required for scanning in the scanning plane would be used as required for the particular implementation.

Figure 5B:
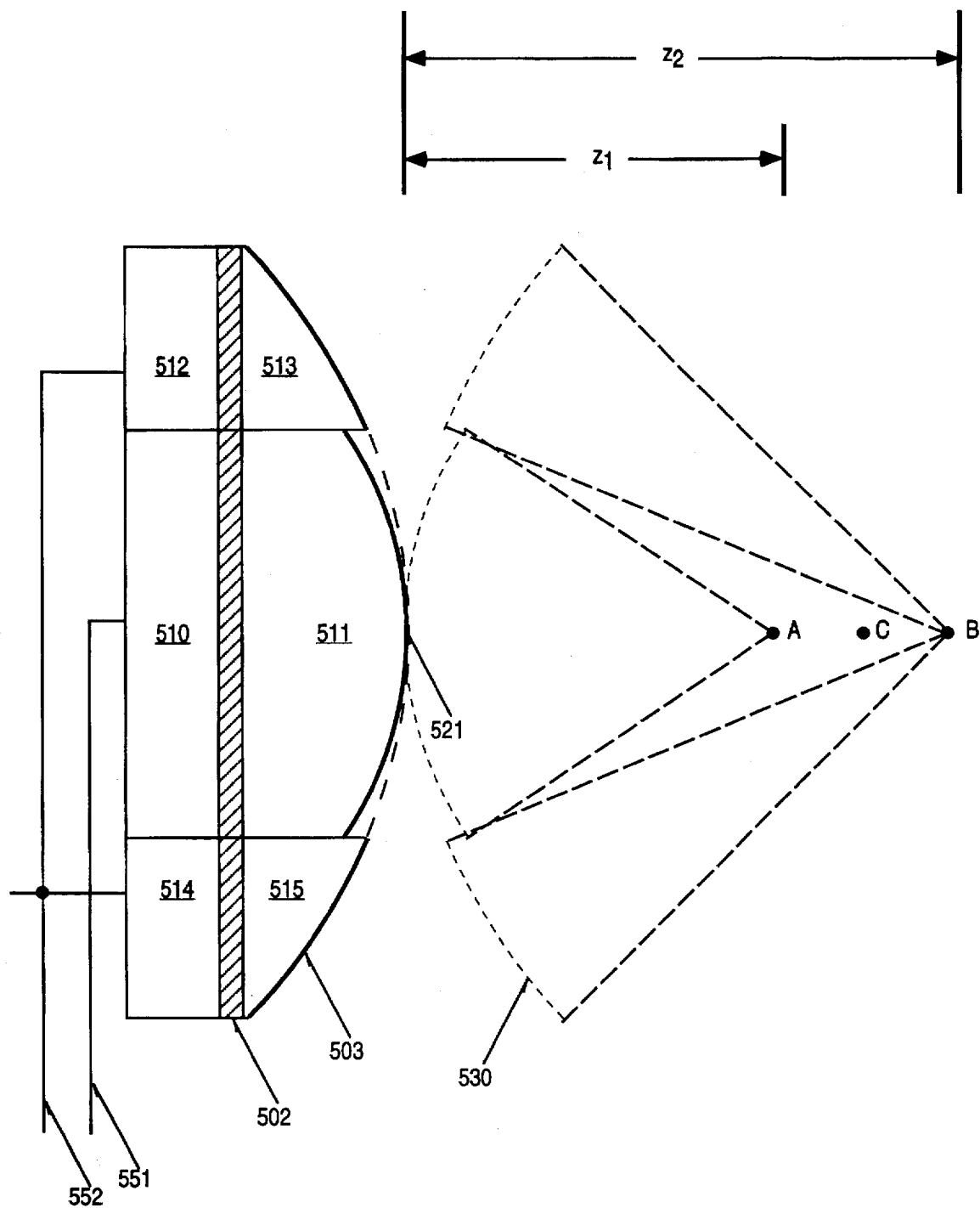

FIG. 5b shows a cross-section of the alternative embodiment 500 of the sparse transducer array in the elevational plane having a compound lens (a lens having more than one preset focal zone). As illustrated, a compound lens 503 is affixed to the sparse transducer array shown as elements 501 using an epoxy or other similar adhesive medium 502. Alternatively, 503 may be molded or cast using well-known prior art techniques. Thus, 500 may comprise a sparse two-dimensional array of flat transducer elements which are constructed in manner similar to those known to those skilled in the art for use as an ultrasonic burst transmissive/receptive surface. As each transducer element is activated, the energy is then focused by compound lens 503 according to the portion of the lens to which the transducer element(s) are affixed. Thus, when element 510 is activated, the energy generated is focused by the portion 511 of lens 503, causing the focusing of the energy at focal zone (the near-field) A shown in FIG. 5b. Likewise, when elements 512 and 514 are activated via channel 552, the portions 513 and 515 of lens 503 cause the ultrasonic burst to be focused at focal zone B (the far-field) shown in FIG. 5b. The wavefront is shown as 530 in FIG. 5b. As is well known to those skilled in the ultrasonic imaging arts, the elements will similarly be activated for a reception period for receipt of ultrasonic echoes due to the ultrasound reference burst(s) following transmission. As discussed with reference to FIG. 4b above, transducer array 500 may also be focused by means of electronic delays in both transmission and reception for an intermediate depth C, keeping element path length errors to a minimum. Note that as with 400 illustrated in FIGS. 4a and 4b, the center 521 of lens portion 511 is coincident with the center which would be formed by the cylindrical shapes of the lens portions 513 and 515. As previously discussed, this provides focusing in the far-field B with aperture growth only and in the absence of electronic delays for transmission or reception. Note further that the mechanical construction may not be required to have coincident center portions of the lens, however, such a design will require electronic delays while activating all elements for focusing in the far-field.

Note that in the embodiments of the present invention shown in FIGS. 4a, 4b, 5a, and 5b, that the transducers have been illustrated as being flat in the scanning plane, and are curved only in the elevational plane. Note that this has been shown for illustration purposes only. A wide variety of transducer constructions, including those curved in the scanning plane, may be implemented using the sparse array in conjunction with the compound lens as in the embodiments of FIGS. 4a, 4b, 5a, and 5b, and such has been not illustrated for the purposes of simplicity. Note that any number of designs for a transducer which utilizes scanning in a scanning plane and requires some focusing in the elevational plane may benefit from the advantages of a transducer construction as illustrated in the figures. In addition, an annular array may also be constructed with more than one preset focal zone which provides the same advantage as a two-dimensional transducer with a compound lens.

Figure 6A:
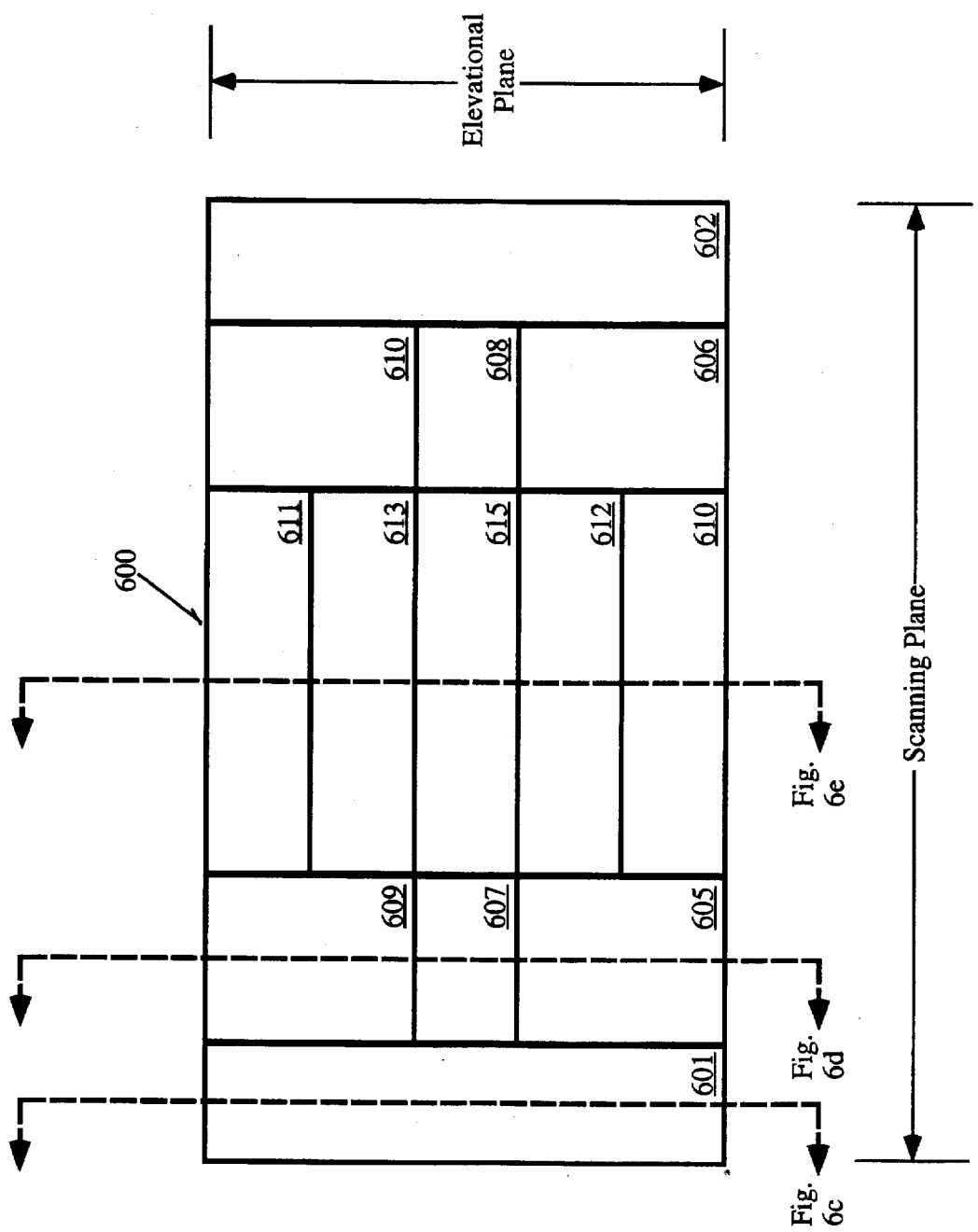
FIGS. 6a–6e show a sparse transducer array with a compound lens which may be affixed to the array and used in an alternative embodiment of the present invention.
Figure 6B:
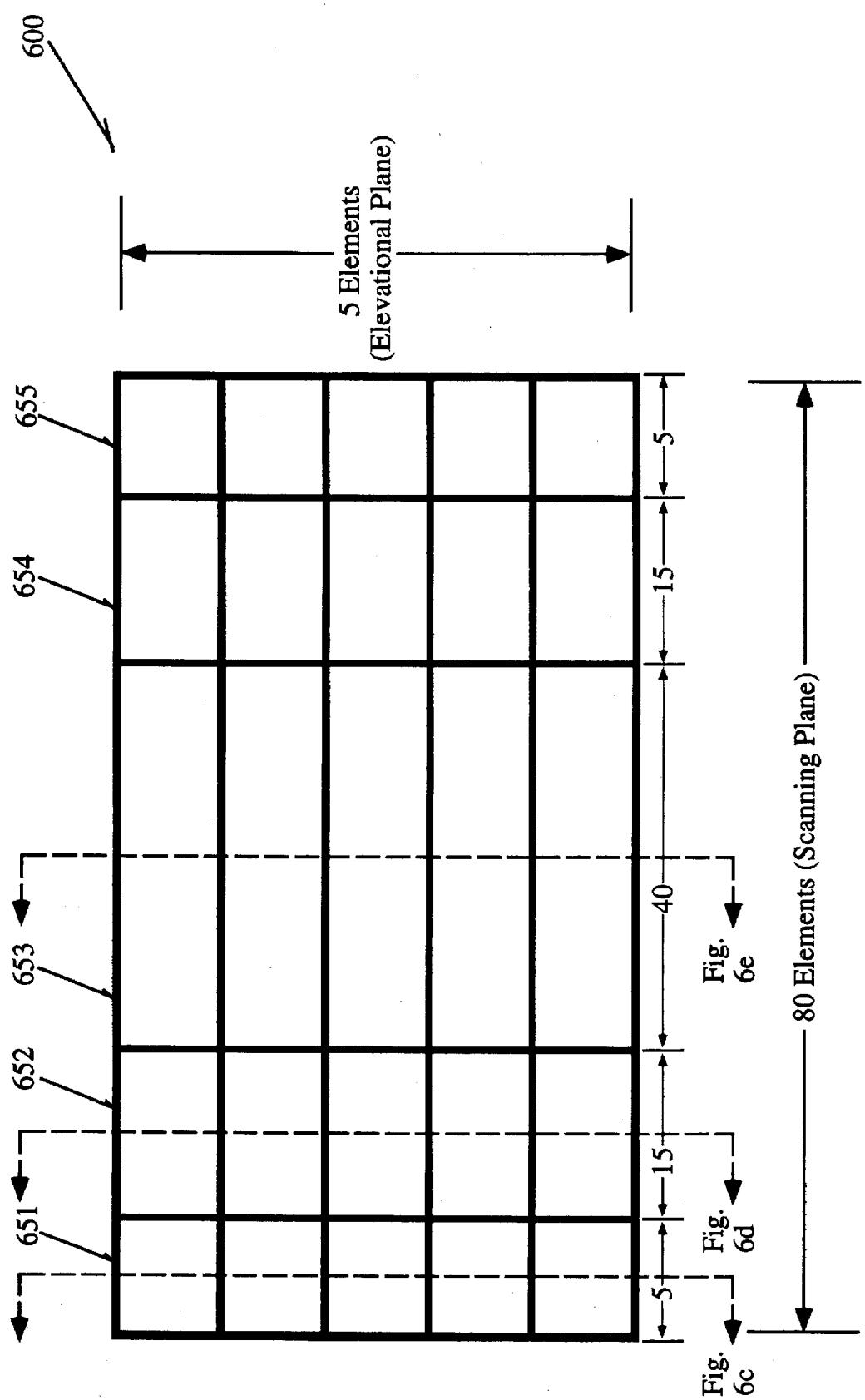
Figure 6C:
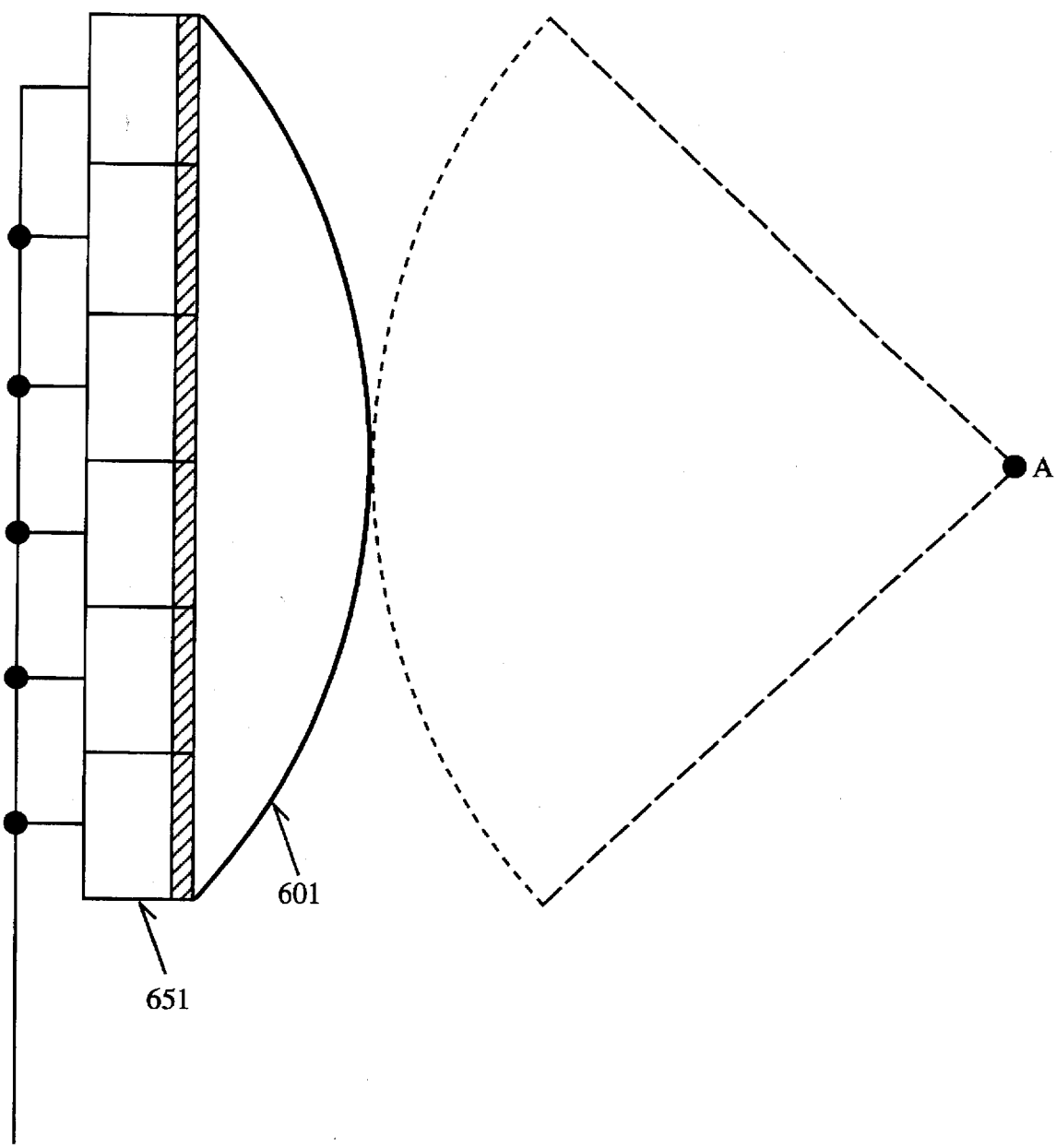
Figure 6D:
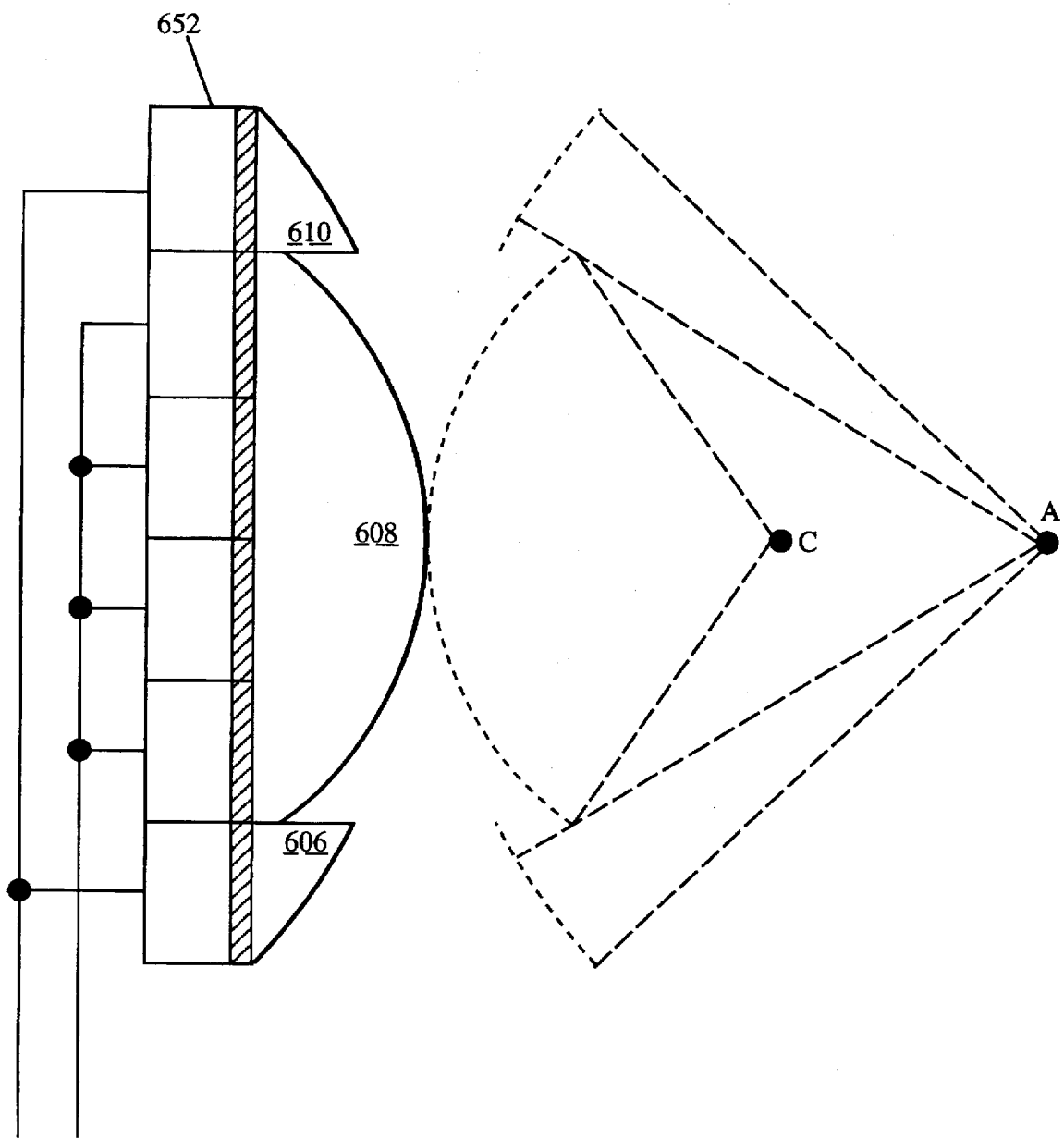
Figure 6E:
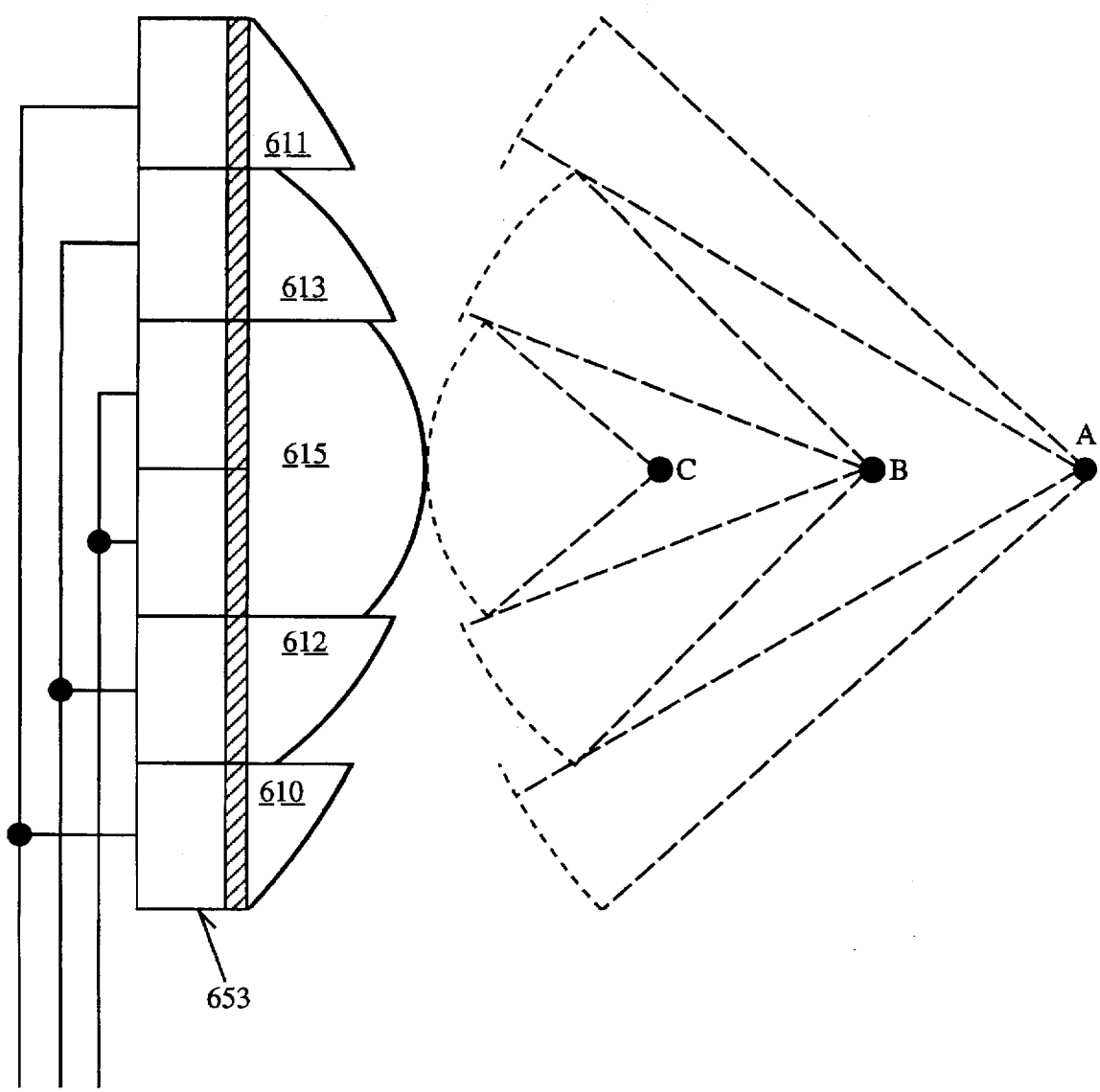

Yet another alternative embodiment of the present invention is illustrated with reference to FIGS. 6a-6e. FIG. 6a shows a front view of a compound lens 600 which may be affixed to a two-dimensional transducer array shown in a front view as 650 in FIG. 6b. 600 of FIG. 6a is a compound lens which is divided into a number of focal regions 601-615 which are constructed and arranged in order to provide different preset focal zones according to the position being scanned. In the embodiment illustrated in FIGS. 6a-6e, the central portions 610-615 of compound lens 600 in the scanning plane have the most focal zones—five separate regions for three separate preset focal zones. 610 and 611 are symmetrically constructed and arranged to have a mechanical focus at a first zone, 612 and 613 have a mechanical focus at a second zone, and central region 615 of the compound lens is constructed to have a third zone. This is shown in FIG. 6e. Sparse transducer elements in the array 650 which are focused by these regions may be wired in parallel, as illustrated in FIG. 6e. Note that the greatest number of focal zones are arranged in the center of the compound lens because during the scanning of the 80 columns across the array the highest resolution is typically required by clinicians in the region of interest (ROI) is in the center of the ROI. Thus, the most focal zones in the elevational plane are provided for enabling the highest resolution in the center of the array.

As illustrated in FIG. 6a, fewer focal zones are provided in areas removed from the central region. For example, during the scanning of elements in regions 652 or 654 of the transducer array, only two focal zones are provided as illustrated in the cross-section view in FIG. 6d. Compound lens 600 has regions 605 and 609 having a predetermined focus at a first position B, and region 607 which has a predetermined focus at a second position A. Similarly, elements 654 which are scanned and focused by regions 606, 608 and 610 have two preset foci. Of course, more focal zones may be provided by using electronic focusing of the five elements in the elevational plane in these zones of array 650, if desired. Finally, at the outer regions of the array only a single fixed focus is provided by compound lens 600 in regions 601 and 602 as illustrated in the cross-section view FIG. 6c. Usually, during ultrasonic examinations of a patient, the periphery of the ROI tend to be of limited interest to the clinician, and therefore, these have only a single mechanical focus, providing less resolution.

Note that the central region 653 of the array has the greatest number of scanning elements (40) in the scanning plane and, thus, the greatest number of elements which are pre-focused at three different focal zones in the elevational plane in this embodiment of the present invention. Again, more focal zones may be provided by electronic focusing. This provides the advantage that the center of the ROI has the highest resolution during imaging. Regions 652 and 654 of the array each have fifteen elements in the scanning plane providing for decreased resolution in those areas. Finally, at the outer regions of the array 651 and 655, only five elements each for providing five separate scanning elements are provided during scanning of those portions of the array. Of course, the present invention may be implemented using focusing both in the scanning plane as well as in the elevational plane, and such capabilities are provided using techniques well-known to those skilled in the art. Thus, using an alternative compound lens such as 600 in conjunction with a sparse transducer array such as 650 comprising 480 separate elements (six in the elevational plane and 80 total in the scanning plane) and thus only 190 separate channels are required (40×3 zones+15×2×2 zones+5×2×1 zone) while taking advantage of symmetrically wired elements in the elevational plane. Specific numbers of transducer elements may vary according to design choice. The highest resolution is thus provided in central areas of a region of interest using two-dimensional scanning of a transducer array in conjunction with a compound lens.

In other embodiments of the present invention, as illustrated above with reference to FIGS. 4a, 4b, 5a, and 5b, a minimum of two mechanically focused focal zones may be provided by the use of a compound lens in conjunction with a sparse array in the elevational plane. This minimizes many of the problems with the prior art, including, but not limited to, keeping element aperture errors to a minimum while providing focusing in the elevational plane. This may be used in combination with any and/or all of the techniques described above to further improve image quality. Other advantages, features and configurations of the compound lens will become apparent to one skilled in the art, and this is not limited by the specific illustrations which have been shown here.

Figure 7:
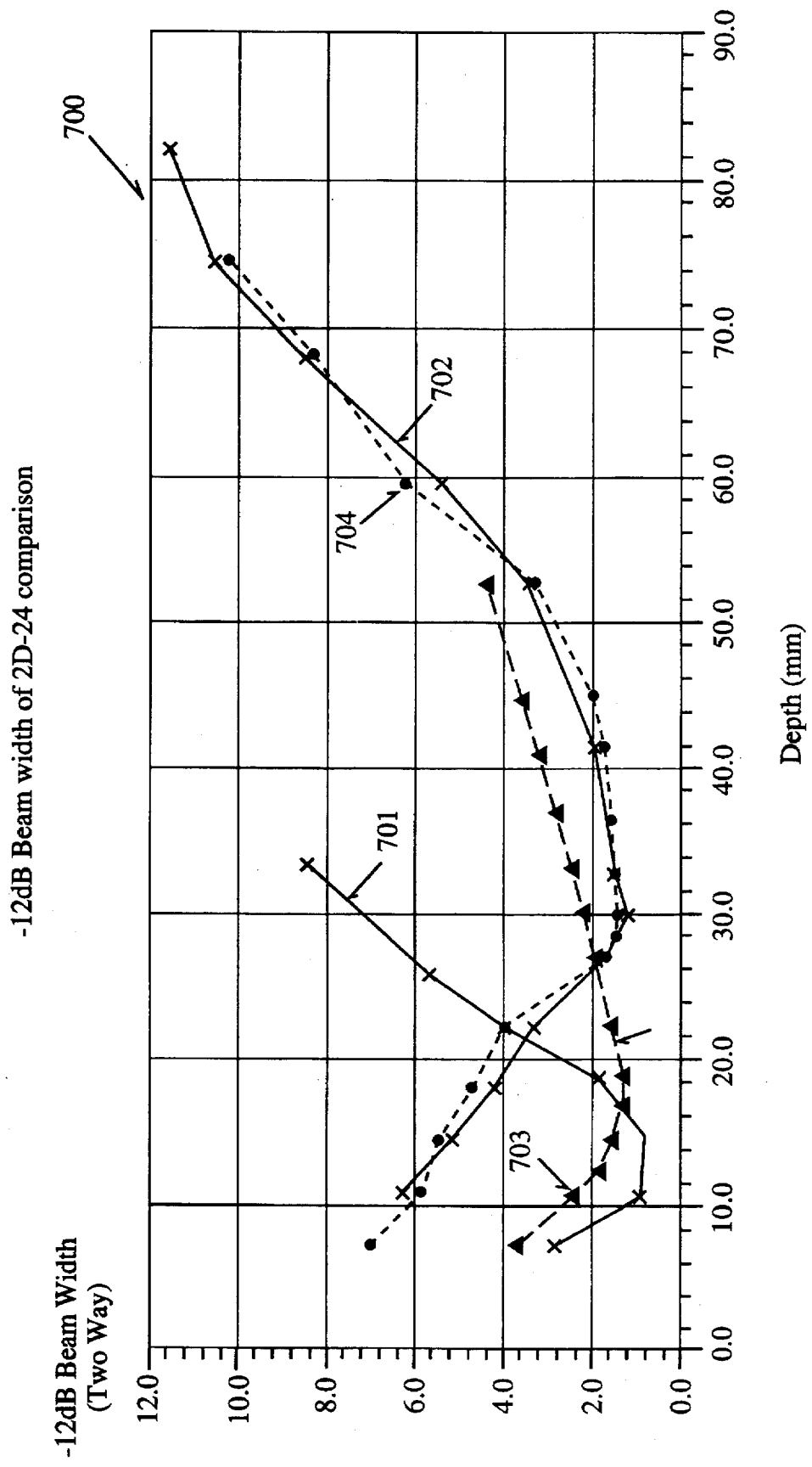
FIG. 7 shows a comparison of the results of using a two-dimensional array with a compound lens versus a prior art transducer.

FIG. 7 shows a comparison of the results of using a two-dimensional array with an implemented compound lens, similar to those described above with reference to FIGS. 4a–6e. The transducer is compared with a typical prior art array which uses existing flat one-dimensional arrays. Plot 701 shows the results of using a typical prior art 5 mm aperture one-dimensional array imaged at a variety of depths. As is clearly apparent, when the prior art array attempts to focus beyond the approximate 15 mm depth within the subject, the beam width increases substantially, as is shown in plot 700. A 4.8 mm aperture lens with a compound array, shown by plot 703, also images nicely in the focal region of 15 mm as shown in the figure due to its mechanical pre-focusing. The prior art 9 mm aperture flat array shown as plot 702 has relatively large beam width at the region of 15 mm because its pre-focusing position is at 30 mm. And as shown by plot 704, the 9 mm aperture with a compound lens has similar focusing characteristic as 702. The sparse two-dimensional transducer array with compound lens combines the advantages of beam plot 703 and 704 so that the focusing of those of plot 703 are used in the region of 15 mm, whereas the focusing of those of plot 704 are used in the region of 30 mm. This results in much longer effective range of focusing in the imaging mechanism. Thus, using the compound lens in conjunction with a sparse two-dimensional array poses substantial advantages over the prior art arrays in the prior an while still providing scanning capabilities.

Figure 8:
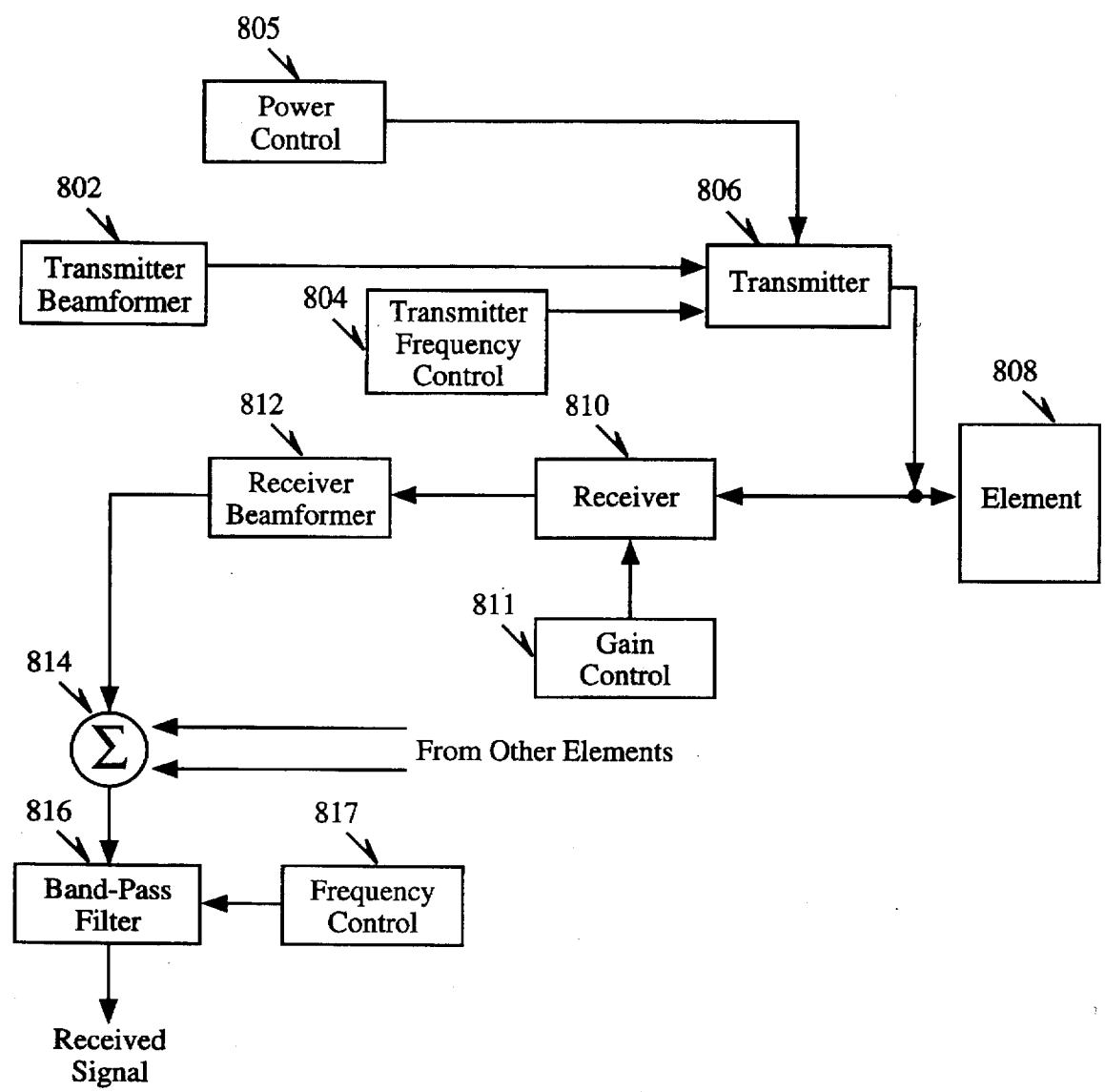
FIG. 8 shows a control circuitry which may be used in conjunction with the sparse two-dimensional arrays as discussed above.

FIG. 8 shows a block diagram of circuitry which may be used in conjunction with any of the sparse transducer arrays of FIG. 4a–6e. The transmit circuitry comprises a transmitter beamformer 802 which controls transmitter 806 in the timing of the transmission of the various elements which are driven by the particular transmitter. The transmitter 806 further has a transmitter frequency control means 804 which produces the appropriate band of the reference pulses. Transmitter 806 is further under control of a power control 805 for adjusting the amplitude of the transmitted signal. Then, the transmitter outputs a signal at the appropriate time delay, amplitude, and frequency band to a single element 808. Note that the transmission circuitry is duplicated for each of the element in the array, in manners well-known to those skilled in the art, however, because the sparse portion of the array is very limited, the circuitry only needs to be duplicated for a small number of channels in the elevational plane.

Reception circuitry is also coupled to the element 808 and is essentially duplicated for as many elements on receive which would be activated at any given time. A receiver 810 receives the RF signals generated by element 808 due to being vibrated due to ultrasonic echoes at the appropriate interval during the receive mode. A gain control 811 controls the appropriate amount of gain to be applied to the signal which is received by receiver 810. The receive signal is then passed to a receiver beamformer 812 which activates the receiver for an appropriate time period after transmission of the reference pulses to form the beam at the appropriate depths. Then, the signal output from receiver beamformer 812 is input to a summing circuit 814 which receives as inputs all elements which are currently being used on this receive. The summed signals are then passed to a band-pass filter circuit 816 which is under control of a frequency control 817 for filtering the signal to receive the signals from the appropriate depth. Then, the band-pass filter 816 generates the appropriate reception signals which are passed to the imaging circuitry in the ultrasonic imaging system. Note that the block diagram in FIG. 8 is shown as an example and is for illustration purposes only, and that any variety of circuitry may be used in conjunction with the sparse arrays described above according to application. For example, some systems may not vary frequency or gain, or vary other parameters according to specific application. Intermediate focal zones in the elevational plane may also not be required to be focused resulting in a very simple elevational plane beamformer in both the transmitter and receiver.

Thus, in conclusion, a sparse two-dimensional transducer array used in conjunction with the compound lens provides numerous advantages over the prior art in both application and function. Although the present invention has been described with reference to some specific embodiments thereof, specifically, with reference to FIGS. 1–8, the present invention should not be viewed as being limited by these specific examples. The present invention therefore is only be limited by the appended claims which follow.

What is claimed is:

1. A two-dimensional ultrasonic transducer for forming images comprising:
   a. a plurality of transducer elements arranged in two dimensions for producing ultrasonic bursts, and receiving reflected ultrasound, said plurality of transducer elements arranged in a two dimensional array in the following manner:
      i. said plurality of transducer elements having a first group of transducer elements arranged in said transducer in a scanning plane in said array, said first group of transducer elements in said scanning plane being arranged to permit scanning;
      ii. said plurality of transducer elements having a second group of transducer elements arranged in said transducer in an elevational plane in said array, said second group of transducer elements having at least two sets of transducer elements symmetrically arranged about an axis parallel to the scanning plane, said two sets of transducer elements shaped differently in said elevational plane in order to have more than one focus at fixed locations; and
   b. one or more conductive channels, each of said one or more conductive channels coupled to one of said at least two sets of symmetrically arranged transducer elements.

2. A two-dimensional ultrasonic transducer for forming images comprising a plurality of transducer elements for producing ultrasonic bursts, and receiving reflected ultrasound due to said ultrasonic bursts, said plurality of transducer elements arranged in an array into columns and rows, said rows of said transducer elements arranged in a scanning plane to permit scanning, each of said columns of said transducer elements having at least two groups of symmetrically arranged transducer elements being oriented in an elevational plane, each of said at least two groups of symmetrically arranged transducer elements being shaped to have a different fixed focus, each of said at least two groups of symmetrically arranged transducer elements coupled to a conductive channel for activating each of said at least two groups of symmetrically arranged transducer elements separately.

3. The ultrasonic transducer of claim 2 wherein said at least two groups of symmetrically arranged transducer elements comprise a first and second group of transducer elements, said first group having a first focus at a first position which is a first distance ($z_1$) from said transducer, and said second group having a second focus at a second position which is a second distance ($z_2$) from said transducer.

4. The ultrasonic transducer of claim 3 wherein the transducer elements in said first group of transducer elements each have a first width ($w_1$) and the transducer elements in said second group of transducer elements each have a second width ($w_2$).

5. The ultrasonic transducer of claim 4 wherein said first distance ($z_1$), said second distance ($z_2$), said first width ($w_1$), and said second width ($w_2$) have the following relationship:

$$z_1/w_1 = z_2/(w_2+w_1).$$

6. The ultrasonic transducer of claim 5 wherein $w_1 = 4.8$ mm, $w_2 = 4.2$ mm, $z_1 = 1.68$ cm and $z_2 = 3$ cm.

7. The ultrasonic transducer of claim 3 wherein said first group of transducer elements is located in a center portion of said columns of said transducer array and said second group of transducer elements is located at symmetrical ends of said columns of said transducer array.

8. The ultrasonic transducer of claim 3 wherein said transducer array further comprises an apparatus coupled to said conductive channel for each of said at least two groups of symmetrically arranged transducer elements for delaying said ultrasonic bursts emitted from certain of said symmetrically arranged transducer elements coupled to said symmetrically arranged transducer elements for focusing at one or more positions other than said first position and said second position.

9. The ultrasonic transducer of claim 2 wherein the width of each of said elements in said columns of said transducer is greater than 4 $\lambda$ wherein $\lambda$ is the wavelength of said ultrasonic bursts.

10. The ultrasonic transducer of claim 2 wherein the width of each of said elements in said columns of said transducer is approximately 6 $\lambda$ wherein $\lambda$ is the wavelength of said ultrasonic bursts.

11. A two-dimensional ultrasonic transducer, said two-dimensional ultrasonic transducer comprising:

a plurality of transducer elements configured to produce ultrasonic bursts, and receive reflected ultrasound, said plurality of transducer elements further arranged as follows a first dimension of said plurality of transducer elements arranged in a scanning plane, a second dimension of said plurality of transducer elements arranged in an elevational plane, the transducer elements in said second dimension being symmetrically arranged with respect to an axis parallel to the scanning plane, one or more transducer elements in said second dimension being shaped to have a first focus, and at least one pair of symmetrical transducer elements in said second dimension being shaped to have a second focus.

12. The two-dimensional ultrasonic transducer of claim 11, wherein said one or more transducer elements define a first cylinder having a first radius, wherein said at least one pair of symmetrical transducer elements define a second cylinder having a second radius, wherein said second radius is larger than said first radius and said first cylinder and said second cylinder share a common point along their respective circumferences.

13. The two-dimensional ultrasonic transducer of claim 11 further comprising one or more channels coupled to said plurality of transducer elements for activating said plurality of transducer elements.

14. The two-dimensional ultrasonic transducer of claim 13 wherein a first channel of said one or more channels is coupled in parallel to said at least one pair of symmetrical transducer elements to allow tandem activation.

* * * * *